United States Patent [19]

Gries et al.

[11] 4,001,298
[45] Jan. 4, 1977

[54] TRIIODIZED N-METHYLDICARBOXYLIC ACID ANILIDES

[75] Inventors: Heinz Gries; Heinrich Pfeiffer, both of Berlin, Germany

[73] Assignee: Schering Aktiengesellschaft, Berlin & Bergkamen, Germany

[22] Filed: Aug. 17, 1972

[21] Appl. No.: 281,379

[30] Foreign Application Priority Data

Aug. 17, 1971 Germany .................. 2141803

[52] U.S. Cl. .................. 260/471 R; 260/239.3 R; 260/293.77; 260/247.2 A; 260/326.85; 260/404.5; 260/516; 260/519; 260/544 N; 260/558 P
[51] Int. Cl.$^2$ .................. C07C 101/50
[58] Field of Search .......... 260/519, 471 R, 544 M, 260/544 C, 544 N

[56] References Cited

UNITED STATES PATENTS 3,542,861 11/1970 Ackerman .................. 260/518 A
3,732,293 5/1973 Ackerman .................. 260/518 A Primary Examiner—Anton H. Sutto
Attorney, Agent, or Firm—Millen, Raptes & White

[57] ABSTRACT

Triiodized N-methyldicarboxylic acid anilides of the Formula

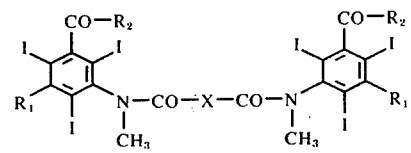

wherein $R_1$ is hydrogen, halogen, carboxyl, N-monoacylamino, N-monoalkoxyacylamino, N-alkyl-N-acylamino, N-alkyl-N-alkoxyacylamino, N,N-diacylamino, N-acylaminomethyl,

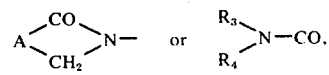

wherein A is alkylene of 2 or 3 carbon atoms which can be interrupted by an oxygen atom, and $R_3$ and $R_4$ are each hydrogen, lower alkyl or hydroxyalkyl, or $R_3$ and $R_4$ together with the nitrogen atom form a 5 to 7 member heterocyclic ring which can contain a further oxygen, nitrogen, or sulfur hetero atom; $R_2$ is halogen, hydroxy, lower alkoxy, hydroxyalkoxy or alkoxyalkoxy; and X is straight or branched alkylene of 2–14 carbon atoms interrupted by one or more oxygen or sulfur atoms, and the salts of these compounds with physiologically compatible bases are valuable radiopaque agents.

14 Claims, No Drawings

TRIIODIZED N-METHYLDICARBOXYLIC ACID ANILIDES

BACKGROUND OF THE INVENTION

1. Field of the Invention

This invention relates to triiodized N-methyldicarboxylic acid anilides and to processes for their preparation and use.

2. Description of the Prior Art

Compounds suitable for use as radiopaque agents, especially for intravenous uro-, angio- and cholegraphy, must meet very high requirements with respect to vascular system compatibility and pharmacological inertness. The triiodated benzoic acids used for uro- and angiography show a considerable osmotic pressure raised by the diagnostically necessary high salt concentration of the injection solutions. Therefore it was already tried to lower the osmotic pressure with retaining the same iodine concentration by linkage of two molecules. However, on the synthesis of these compounds considerable difficulties araised, which, for instance, resulted in low yields, e.g., U.S. Pat. No. 3,542,861.

OBJECTS OF THE INVENTION

Accordingly, it is an object of this invention to provide novel triiodized N-methyldicarboxylic acid anilides.

Another object of this invention is to provide a process for preparing triiodized N-methyldicarboxylic acid anilides in good yields.

A further object of this invention is to provide useful radiopaque compositions and methods for their use.

Upon further study of the specification and apended claims, further objects and advantages of this invention will become apparent to those skilled in the art.

SUMMARY OF THE INVENTION

Briefly, the above and other objects of this invention are attained in one aspect by providing a compound of Formula I

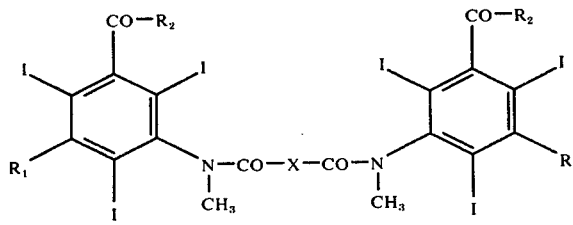

wherein $R_1$ is hydrogen, halogen, carboxyl, N-monoacylamino, N-monoalkoxyacylamino, N-alkyl-N-acylamino, N-alkyl-N-alkoxyacylamino, N,N-diacylamino, N-acylaminomethyl, $$A\begin{matrix}CO\\ \\CH_2\end{matrix}\!\!>\!\!N- \quad \text{or} \quad \begin{matrix}R_3\\ \\R_4\end{matrix}\!\!>\!\!N-CO,$$

wherein A is alkylene of 2 or 3 carbon atoms which can be interrupted by an oxygen atom and $R_3$ and $R_4$ each are hydrogen, lower akyl or hydroxyalkyl, or $R_3$ and $R_4$ together with the nitrogen atom form a 5 to 7 member heterocyclic ring which can contain a further oxygen, nitrogen, or sulfur hetero atom; $R_2$ is halogen, hydroxy, lower alkoxy, hydroxyalkoxy or alkoxyalkoxy; and X is straight or branched alkylene of 2–14 carbon atoms interrupted by one or more oxygen or sulfur atoms, and their physiologically acceptable salts.

In another aspect, compounds of Formula I are prepared by a process which comprises reacting a compound of Formula II wherein $R_1$ has the above-indicated values and $R_2$ is halogen, hydroxy, lower alkoxy or alkoxyalkoxy group, with a dicarboxylic acid dihalide derivative of Formula III $$\text{Hal} - \text{CO} - \text{X} - \text{CO} - \text{Hal} \qquad \text{III}$$

wherein X has the above-indicated values and Hal is chlorine or bromine.

DETAILED DISCUSSION

The compounds of this invention according to Formula I include both the free compounds and their metal, ammonium and amine salts, preferably the water-soluble and non-toxic physiologically acceptable salts. These compounds, individually or in admixture, are valuable radiopaque agents.

The alkyl, alkoxy, and acyl residues when present are preferably lower residues, e.g., lower alkyl of 1–6 carbon atoms, preferably 1–4 carbon atoms such as methyl, ethyl, propyl, isopropyl, or butyl; lower alkoxy of 1–4 carbon atoms, preferably 1–2 carbon atoms, such as methoxy or ethoxy; lower acyl, preferably lower alkanoyl of 1 – 6 carbon atoms, and especially lower alkanoyl of 1–4 carbon atoms such as acetyl, propionyl, butyryl, isobutryl, valeryl and hexanoyl.

Suitable salts of physiologically compatible bases include but are not limited to the alkali metal salts, e.g., sodium and lithium; the alkaline earth metal salts, e.g., calcium and magnesium; amine salts, e.g., ammonium, heterocyclic amines, e.g., morpholine and N-alkyl amines hydroxyalkylamines, alkyl(hydroxyalkyl)amines and di(hydroxyalkyl)amines, wherein alkyl in each instance preferably contains 1–6, more preferably 1–4 carbon atoms, e.g., methyl, ethyl, n-propyl, 2-propyl, n-butyl, isobutyl, tert.-butyl, including trimethylamine, diethylamine, ethanolamine, diethanolamine and polyhydroxyalkylamines, e.g., trihydroxy-tert.-butylamine, saccharidyl amines, including glucamine, N-monoalkylglucamines and N,N-dialkylglucamines. Preferred mono- and dialkyl glucamines are those compounds which contain, in one or both alkyl groups respectively, a total of one to four carbon atoms. Especially preferred alkylglucamine salts are the N-methyl and N,N-dimethyl salts.

Generally, compounds of Formula I are those in which $R_1$ is hydrogen, halogen (preferably chlorine), carboxyl, N-monoalkanoylamino, N-monoalkoxyalkanoylamino, N-alkyl-N-alkanoylamino, N-alkyl-N- alkoxyalkanoylamino, N,N-dialkanoylamino, N-alkanoylaminomethyl,

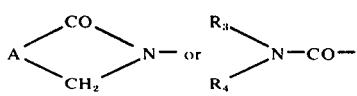

wherein A is alkylene of 2 or 3 carbon atoms and $R_3$ and $R_4$ are each hydrogen, lower alkyl or hydroxyalkyl, or $R_3$ and $R_4$ together with the nitrogen atom forms a 5 to 7 member heterocyclic ring; $R_2$ is halogen (preferably chlorine), hydroxy, lower alkoxy, hydroxyalkoxy or alkoxyalkoxy; and X is alkylene of 2–14 carbon atoms interrupted by at least one oxygen atom. Preferably, the designation "alk" as used herein in each instance refers to a lower alkyl group, i.e., of 1–6 carbon atoms.

Preferred compounds of this invention are those of Formula I meeting one or more of the following definitions:

a. Compounds wherein $R_1$ is hydrogen, chlorine, N-lower alkanoylamino or N-lower alkyl-N-lower akanoylamino;

b. Compounds wherein $R_2$ is chlorine, hydroxy, or lower alkoxy of 1–4 carbon atoms;

c. Compounds wherein $R_3$ and $R_4$ are each alkyl or hydroxyalkyl of 1–4 carbon atoms or hydrogen;

d. Compounds wherein $R_3$ and $R_4$ together with the nitrogen atom form a 5 to 7 member heterocyclic ring containing 0–1 further oxygen atoms, e.g., a morpholine or pyrrolidine ring;

e. Compounds wherein X is alkylene of 2–6 carbon atoms interrupted by a single oxygen or sulfur atom, the sulfur atom when present being preferably but not necessarily present in the reduced bivalent state;

f. Compounds wherein X is alkylene of 2–14 carbon atoms interrupted at every second or third carbon atom by an oxygen or sulfur atom; and g. The di-(2,4,6-triiodo-3-carboxy-N-methylanilides) of diglycolic acid, thiodiglycolic acid, dioxasuberic acid, trioxaundecanedioic acid, and tetraoxahexadecane 1,16-dioic acid.

Specific compounds of Formula I, in addition to those shown in the Examples, include 3,6-dioxasuberic acid di-(3-carboxy-5-dimethylaminocarbonyl-2,4,6-triiodo-N-methylanilide),
diglycolic acid di-(3-carboxy-5-acetylamino-2,4,6-triiodo-N-methylanilide),
diglycolic acid di-(3-carboxy-5-methoxyacetylamino-2,4,6-triiodo-N-methylanilide),
sulfonyldipropionic acid di-(3-carboxy-5-N-methyl-N-methoxyacetylamino-2,4,6-triiodo-N-methylanilide),
4-oxapimelic acid di-(3-carboxy-5-piperidinocarbonyl-2,4,6-triiodo-N-methylanilide),
3,6-dioxasuberic acid di-(3-carboxy-5-propionylaminomethyl-2,4,6-triiodo-N-methylanilide),
4,8-dioxaundecandioic acid di-(3-carboxy-5-N-ethyl-N-acetylamino-2,4,6-triiodo-N-methylanilide),
diglycolic acid di-(3-carboxy-5-morpholinocarbonyl-2,4,6-triiodo-N-methylanilide),
diglycolic acid di-(3-carboxy-5-buturylaminomethyl-2,4,6-triiodo-N-methylanilide);

Equivalents of the compounds of this invention wherein $R_1$ is a group bearing a lower-alkanoyl group are compounds otherwise corresponding structurally thereto and possessing the same activity where instead of a lower-alkanoyl group there is present the acyl group of another organic acid, e.g., a carboxylic-acid containing up to 15 carbon atoms, especially lower (1–6) carbon atoms and intermediate (7–12) aliphatic carboxylic, preferably an alkanoic acid, which can be unsaturated, branched, polybasic, or substituted in the usual manner, e.g., by hydroxy or halogen atoms; a cycloaliphatic, aromatic and mixed aromatic-aliphatic (alkaryl and aralkyl) acid, which can likewise be substituted in the usual manner, examples of preferred acids being acetic acid, propionic acid, caproic acid, enanthic acid, undecyclic acid, oleic acid, trimethylacetic acid, dichloroacetic acid, cyclopentylpropionic acid, phenylpropionic acid, phenylacetic acid, phenoxyacetic acid, succinic acid, benzoic acid; others being acids containing 1–18, preferably 2–12 carbon atoms, including an aliphatic acid containing 1–18, preferably 1–6 carbon atoms, e.g., formic, butyric, isobutyric, α-ethylbutyric, valeric, isovaleric, α-ethylvaleric, 2-methylbutyric, 3-ethylbutyric, hexanoic, diethylacetic, triethylacetic, enanthic, octanoic, undecyclic and palmitic acid; a cyclic acid, preferably a cycloaliphatic acid, containing 5–18 carbon atoms, e.g., cyclopropylideneacetic, cyclobutylcarboxylic, cyclopentylcarboxylic, cyclopentylacetic, cyclohexyl carboxylic, cyclohexylacetic and β-cyclohexylpropionic acid; a carbocyclic aryl or alkaryl acid containing 6–18 carbon atoms, 1 or 2 rings, e.g., benzoic, 2-, 3-, or 4-methylbenzoic, 2,3-, 2,4-, 2,5-, 2,6-, 3,4-, and 3,5-dimethylbenzoic, ethylbenzoic, 2,3,6-trimethylbenzoic, and 3-methyl-α-naphthoic acid; an aralkyl acid containing 7 to 18 carbon atoms, e.g., β-phenylpropionic; a polybasic acid containing 2–18 carbon atoms and 1 to 5 hydroxy groups, e.g., glycolic, lactic, citric, tartaric, d-maleic, d-glyceric, and salicyclic acid; the corresponding acids containing one, two or more of simple substituents, e.g., halo, alkoxy, acyloxy, etc., in the molecule, e.g., chloroacetic, fluoroacetic, trichloroacetic, trifluoroacetic, 2,3,4-trimethoxybenzoic, phenoxyacetic, α-naphthoxyacetic acid, etc.

The acyl group of such equivalent compounds can also be that of a sulfonic acid, e.g., an arylsulfonic, including benzenesulfonic, p-toluene-sulfonic, m,m'-dimethylbenzenesulfonic, o,o'-dimethylbenzenesulfonic, sym.-trimethylbenzenesulfonic, sym.-triethylbenzenesulfonic, m-ethylbenzenesulfonic, para-isopropylbenzenesulfonic, m-n-butylbenzenesulfonic acid, or an alkylsulfonic, e.g., methanesulfonic, ethanesulfonic, propanesulfonic, isopropanesulfonic, butanesulfonic, tert.-butanesulfonic, pentanesulfonic, isopentanesulfonic, hexanesulfonic, heptanesulfonic, octylsulfonic or heterocyclic sulfonic, e.g., α-pyridinesulfonic, α-pyranesulfonic, α-thiophensulfonic, α-furansulfonic, α-tetrahydrofuransulfonic, or other alkyl-,, carbocyclic and heterocyclic aryl-, alkaryl-and aralkyl-sulfonic acid, preferably one containing 1–8 carbon atoms and 0–2, preferably 0–1 N, S or O heteroatoms, which are preferably ring carbon atoms in a heterocyclic ring.

The invention furthermore relates to a process for the production of compounds of Formula I, characterized in that a compound of Formula II

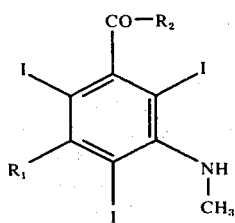

II

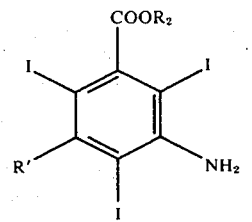

IV wherein $R_1$ has the above-indicated values and $R_2$ is halogen, hydroxy, lower alkoxy or alkoxyalkoxy group, is reacted with a dicarboxylic acid dihalide derivative of Formula III

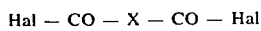

III wherein X has the above-indicated values and Hal is chlorine or bromine.

Depending on the desired value for $R_2$ in the final product, the primarily obtained compounds wherein $R_2$ = halogen are optionally saponified or converted, with lower alcohols, hydroxyalcohols or alkoxyalcohols, into the esters of Formula I; and/or compounds wherein $R_2$ = OH are esterified or converted into the corresponding salts by neutralization with physiologically compatible bases.

The reaction of an acid halide of Formula II ($R_2$ = halogen) with a dicarboxylic acid derivative of Formula III is preferably conducted by heating the reactants in an inert solvent, i.e., a solvent which dissolves the reactants without adversely affecting the course of the reaction, to a temperature of about 80°–150° C. Suitable inert solvents include but are not limited to chlorobenzene and toluene.

The reaction of an acid of Formula II ($R_2$ = OH) or a corresponding ester ($R_2$ = alkoxy) with a dicarboxylic acid derivative of Formula III is preferably effected in an inert solvent at slightly lower temperatures, e.g., at temperatures of 60° – 140° C. Suitable inert solvents include but are not limited to dioxane, toluene, dimethylformamide and dimethylacetamide.

It was totally unexpected that the condensation reaction of this invention of a compound according to Formula II with a dicarboxylic acid dihalide of Formula III would take place with such high yields. To the contrary, it is known that the yields in the analogous reaction starting with 3-amino-2,4,6-triiodobenzoic acids substituted in the 5-position, are considerably lower. Therefore, it was surprising that such a favorable yield is attained in the course of the reaction, presumably due to the monomethylation of the amino group in the 3-position.

The monomethylamino compounds utilized as starting substances according to Formula II can be produced from the corresponding amino compounds by methylation, e.g., with formaldehyde and sulfuric acid, preferably by the methylating process which is more particularly described in copending U.S. pat. application Ser. No. 184,941, filed Sept. 29, 1971, now U.S. Pat. No. 3,883,578, the contents of which are incorporated by reference herein.

Briefly, compounds of Formula IV wherein R' is hydrogen or iodine, or an amino, monoacylamino, mono alkoxyacylamino, alkylacylamino, N-alkyl-N-alkoxy acylamino, diacylamino, acylaminomethyl,

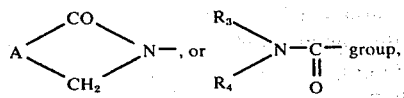

wherein A, $R_2$, $R_3$, and $R_4$ have the above-indicated meanings, are treated with a mixture of sulfuric acid and formaldehyde and, depending on the finally desired meaning of $R_2$, the thus-obtained compounds are optionally saponified, esterified, or converted into the salts.

The formaldehyde employed as the methylating agent can be utilized in the form of monomeric or polymeric formaldehyde, or as an aqueous formalin solution. The sulfuric acid is preferably used in the concentrated form. In order to obtain as complete a monomethylation as possible, it is advantageous to utilize the formaldehyde in an excess. The reaction can be conducted in a temperature range of about 30° C. to 80° C. After about 2–10 hours at 40°–60° C., the reaction is terminated. The final product is isolated in the customary manner, for example by precipitation with ice water and optionally by extraction with a suitable solvent.

Compounds of Formula II wherein $R_2$ = halogen can also be obtained from the corresponding compounds of general Formula II with $R_2$ = hydroxy by conventional halogenation reactions.

The novel triiodized N-methyldicarboxylic acid anilide derivatives of Formula I are valuable contrast agents for radiopaque materials and novel intermediates for the production of radiological contrast substances. For example, the compounds of general Formula I wherein $R_2$ is halogen can be saponified to the corresponding acids or reacted with alcohol to form the corresponding esters.

The compounds of this invention can be employed in mixture with conventional excipients, i.e., pharmaceutically acceptable organic or inorganic carrier substances suitable for parenteral or enteral application which do not deleteriously react with the active compounds. Suitable pharmaceutically acceptable carriers include but are not limited to water, salt solutions, alcohols, vegetable oils, polyethylene glycols, gelatin, lactose, amylose, magnesium stearate, viscous paraffin, perfume oil, fatty acid monoglycerides and diglycerides, pentaerythritol fatty acid esters, hydroxy methylcellulose, polyvinyl pyrrolidone, talc, etc.

For parenteral application, particularly suitable are solutions, preferably oily or aqueous solutions, as well as suspensions or emulsions. Ampoules are convenient unit dosages.

For enteral application, particularly suitable are tablets or dragees having talc and/or a carbohydrate carrier or binder or the like, the carrier preferably being lactose and/or corn starch and/or potato starch. A syrup or the like can be used wherein a sweetened vehicle is employed. Sustained release compositions can also be formulated wherein the active compound is protected with differentially degradable coatings, e.g., by microencapsulation, multiple coatings, etc.

For intravenous administration the soluble salts of this invention are preferably used in aqueous solution whereby the concentration of the salts is preferably between about 15% by volume and about 75 % by volume. Generally the amount of active agent per unit dosage is about 5 to 50 g, preferably 7 to 35 g.

The acids, in the form of their water-soluble, physiologically compatible salts, are extraordinarily good radiopaque agents for urography, angiography, and cholecystography. The salt solutions are characterized by an relative low viscosity and can be administered by intravenous injection. The salt solutions are furthermore distinguished by a good circulatory compatibility and a low toxicity. The esters of Formula I are suitable as bronchographic agents.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, the temperatures are set forth in degrees Celsius. Unless otherwise indicated, all parts and percentages are by weight.

EXAMPLE 1

144 g. of hydrochloride of 3-methylamino-2,4,6-triiodobenzoyl chloride (m.p. 249°–251° under decomposition, produced from 148 g. of 3-methylamino-2,4,6-triiodobenzoic acid and 595 ml. of thionyl chloride at 50°–55°) is dissolved in 1.4 l. of boiling chlorobenzene. A solution of 34.5 g. of diglycolic acid dichloride in 35 ml. of chlorobenzene is added dropwise thereto. After refluxing for three hours, the reaction mixture is concentrated to dryness, and the residue is recrystallized from ten times the amount of tetrahydrofuran, thus obtaining 125 g. (86% of theory) of the di-(3-chlorocarbonyl-2,4,6-triiodo-N-methylanilide) of diglycolic acid, m.p. 249°–251° (under decomposition).

EXAMPLE 2

At 80°, a solution of 6.5 g. of diglycolic acid dichloride in 20 ml. of dioxane is added dropwise to a solution of 35 g. of 3-methylamino-2,4,6-triiodobenzoic acid in 50 ml. of dioxane. After 30 minutes, the reaction temperature is increased to 95°; thereafter, the reaction mixture is held at this temperature for 4 hours. Then, the mixture is precipitated into ice water (2.5 l.) and the thus-formed precipitate is vacuum-filtered, washed with water, and dried at 50°. For the removal of impurities, the reaction product is extracted twice with respectively 150 ml. of ethyl acetate. The remainder is dried at 50° and suspended in 500 ml. of water. By the addition of dilute solution of sodium hydroxide, a solution of the disodium salt is prepared which is clarified and decolorized with 5 g. of activated carbon. After filtration, the product is precipitated by adding hydrochloric acid, the precipitate is vacuum-filtered, washed free of chloride with water, and dried at 50°, thus obtaining 21 g. (54.5% of theory) of diglycolic acid di-(3-carboxy-2;4,6-triiodo-N-methylanilide), m.p. 260° (under decomposition).

EXAMPLE 3

30 g. of 3-methylamino-2,4,6-triiodobenzoic acid in dissolved in 45 ml. of dioxane at 80°. Then, a solution of 8.5 g. of 3,6,9-trioxaundecanedioic acid dichloride in 20 ml. of dioxane is added dropwise thereto, and the mixture is maintained at 90°–95° for 3 hours. After cooling, the reaction mixture is poured into 2 l. of ice water, agitated for 3 hours in the ice bath, and the thus-separated precipitate is vacuum-filtered. After washing with water and drying at 50°, the reaction product is dissolved in aqueous sodium hydroxide solution. The solution is stirred for 30 minutes with 5 g. of activated carbon, filtered, brought to a pH of 5 – 5.5 by the addition of glacial acetic acid, treated again with 5 g. of activated carbon, filtered, and precipitated by the addition of concentrated hydrochloric acid at a pH of 1. After filtering the precipitate, washing with water, and drying at 5020 , 23 g. (72% of theory) of 3,6,9-trioxaundecanedioic acid di-(3-carboxy-2,4,6-triiodo-N-methylanilide) is obtained, m.p. 167°–171° (under decomposition).

EXAMPLE 4

99.5 g. of 3-methylamino-5-acetylaminomethyl-2,4,6-triiodobenzoic acid is suspended in 350 ml. of dioxane. The suspension is heated to 80°, and a solution of 16.5 g. of diglycolic acid dichloride in 55 ml. of dioxane is added dropwise thereto within 10 minutes under agitation. Thereafter, the reaction mixture is maintained for 4 hours at 95°. After cooling to room temperature, the mixture is poured into 3 l. of ice water, stirred for 30 minutes, and the thus-separated precipitate is vacuum-filtered, washed with water, and dried at 50°. The thus-produced crude product (95 g.) is suspended in 350 ml. of ethanol and dissolved by adding 60 ml. of anhydrous diethylamine. After stirring overnight, the separated diethylamine salt is vacuum-filtered, washed with ethanol, and dried under vacuum, wherafter it is dissolved in 1 l. of water, and 5 g. of activated carbon is added for decolorizing purposes. After filtration, the solution is brought to a pH of 1 by adding concentrated hydrochloric acid. After several hours of agitation in an ice bath, the precipitate is vacuum-filtered, washed with water, and dried at 50°, thus obtaining 84 g. of diglycolic acid di-(3-carboxy-5-acetylaminomethyl-2,4,6-triiodo-N-methylanilide), m.p. 245°–248° (under decomposition).

EXAMPLE 5

A solution of 20 g. of thiodiglycolic acid dichloride in 40 ml. of dioxane is added dropwise within 10 minutes to a solution of 52.9 g. of 3-methylamino-2,4,6-triiodobenzoic acid in 75 ml. of dioxane at 80°. Then, the reaction mixture is maintained at 100° C. for 6 hours, cooled to room temperature, and 3 l. of ice water is gradually added dropwise under stirring and cooling. The mixture is further agitated for several hours under ice cooling, and then the separated precipitate is filtered off. After drying at 50°, the thus-obtained crude product (55 g.) is suspended in 500 ml. of water and dissolved at a pH of 11 by the addition of semiconcentrated sodium hydroxide solution. After filtration over 5 g. of activated carbon, the clear solution, having a yellowish brown color, is adjusted to pH 5.5 with acetic acid and decolorized by several treatments with respectively 2 g. of activated carbon. The colorless filtrate is brought to pH 1 by the addition of dilute hydrochloric acid under ice cooling, and the thus-separated precipitate is vacuum-filtered after several hours of agitation, washed with water, and dried at 50°.

In this way, 51 g. (87.5% of theory) of thiodiglycolic acid di-(3- carboxy-2,4,6-triiodo-N-methylanilide) is produced, m.p. 266°–268° (under decomposition).

EXAMPLE 6

A solution of 18.5 g. of diglycolic acid dichloride in 30 ml. of dioxane is added dropwise to a solution of 60 g. of 3-methylamino-5-N-methlacetylamino-2,4,6-triiodobenzoic acid in 250 ml. of dioxane at 80°. The reaction mixture is maintained at 95°–100° for several hours until the evolution of hydrogen chloride has ceased. After cooling to room temperature, the mixture is poured into 3 l. of ice water under agitation, and the filtered precipitate is dried at 50°. The thus-obtained crude product (63 g.) is purified by treating the aqueous solution of the disodium salt several times with activated carbon. After precipitation with hydrochloric acid, vacuum-filtering, washing with water, and drying at 50°,59 g. (91% of theory) of diglycolic acid di-(3-carboxy-5-N-methyl-N-acetylamino-2,4,6-triiodo-N-methylanilide) is obtained, m.p. 254°–256° (under decomposition).

EXAMPLE 7

13.5 g. of 3-methylamino-2,4,6-triiodobenzoic acid methyl ester is dissolved in the hot state in 40 ml. of toluene. Then, a solution of 2.8 g. of diglycolic acid dichloride in 10 ml. of toluene is added dropwise to the boiling solution. The evolution of hydrogen chloride starts rapidly, and after some time, the reaction product is being precipitated. In order to complete the reaction, the charge is maintained under reflux for 8 hours, and then 20 ml. of toluene is distilled off and the mixture is allowed to stand at room temperature overnight. The thus-crystallized condensation product is vacuum-filtered, washed with toluene, and dried at 50°, thus obtaining 11.5 g. (74% of theory) of diglycolic acid di-(3-methoxycarbonyl-2,4,6-triiodo-N-methylanilide), m.p. 253°–256° (under decomposition).

EXAMPLE 8

28.6 g. of 3-methylamino-2,4,6-triiodoisophthalic acid is dissolved in the hot state in a mixture of 120 ml. of dioxane and 120 ml. of toluene. Then, a solution of 5.1 g. of diglycolic acid dichloride in 10 ml. of toluene is added dropwise to the boiling solution. The mixture is heated for 6 hours under reflux, allowed to cool to room temperature, and the thus-precipitated reaction product is separated, washed with hot toluene, and dried at 50°. The thus-obtained crude product (27 g.) is dissolved as the tetrasodium salt in the aqueous phase and the solution decolorized by several treatments with activated carbon. Then, the solution is gradually allowed to flow into hot concentrated hydrochloric acid, whereby a white, curdy precipitate is separated. The latter is vacuum-filtered, washed with water, and dried at 50°, thus obtaining 25 g. (81% of theory) of diglycolic acid di-(3,5-dicarboxy-2,4,6-triiodo-N-methylanilide), m.p. 257°–260° (under decomposition).

EXAMPLE 9

120 g. of diglycolic acid di-(3-chlorocarbonyl-2,4,6-triiodo-N-methylanilide) obtained according to Example 1 is dissolved in 1.2 l. of dioxane at 80°. Then, 500 ml. of water and 145 ml. of concentrated sodium hydroxide solution are gradually added thereto and the mixture allowed to react for 1 hour at 90°. Then, 10 g. of activated carbon is added, the mixture is vacuum-filtered, and the solution is concentrated under vacuum to about 500 ml. Thereafter, the solution is diluted with 1 l. of water, and the saponification product is precipitated under agitation and cooling in an ice bath by the addition of semiconcentratd sulfuric acid. After vacuum-filtering, washing with water, and drying at 50°, 105 g. (90% of theory) of diglycolic acid di-(3-carboxy-2,4,6-triiodo-N-methylanilide) is obtained, identical with the product prepared according to Example 2.

EXAMPLE 10

14 g. of diglycolic acid di-(3-chlorocarbonyl-2,4,6-triiodo-N-methylanilide) obtained according to Example 1 is dissolved in boiling dimethyl sulfoxide in as concentrated a form as possible. Then, 100 ml. of methanol is added in increments, and the clear solution is heated for 8 hours on steam bath. The reaction mixture is concentrated to dryness and the residue mixed with 100 ml. of 5% by weight soda solution. After several hours of agitation, the residue is vacuum-filtered, washed with water, and dried at 50°, thus producing 11.9 g. (86% of theory) of diglycolic acid di-(3-methoxycarbonyl-2,4,6-triiodo-N-methylanilide), identical with the product obtained in accordance with Example 7.

EXAMPLE 11

26.4 g. of 3-methylamino-2,4,6-triiodobenzoic acid is dissolved in the hot state in 300 ml. of toluene and mixed dropwise within 10 minutes with a solution of 9.8 g. of 4,7,10,13-tetraoxahexadecane-1,16-dioic acid dichloride in 30 ml. of toluene. The reaction mixture is maintained under reflux for 5 hours and then allowed to cool to room temperature under agitation. The thus-separated reaction product is suspended in 200 ml. of water and dissolved by the addition of dilute solution of sodium hydroxide. Five grams of activated carbon is added to the solution, and the latter is agitated for 30 minutes, filtered, the filtrate brought to pH 5.5 by the addition of glacial acetic acid, again treated with 5 g. of activated carbon, filtered, and precipitated by the addition of concentrated hydrochloric acid to a pH of 1. After stirring the mixture for several hours in an ice bath, the thus-separated precipitate is vacuum-filtered, washed with water, and dried under vacuum at room temperature, thus obtaining 27.6 g. (84% of theory) of 4,7,10,13-tetraoxahexadecane-1,16-dioic acid di-(3-carboxy-2,4,6-triiodo-N-methylanilide), m.p. 95°.

EXAMPLE 12

8.7 g. of 3-methylamino-5-chloro-2,4,6-triiodobenzoic acid is dissolved in the hot state in 20 ml. of dioxane and mixed dropwise with a solution of 1.75 g. of diglycolic acid dichloride in 5 ml. of dioxane. The reaction mixture is refluxed until the evolution of hydrogen chloride is terminated, then cooled to room temperature, and 20 ml. of a 5% by weight sodium hydroxide solution is added. The mixture is concentrated to dryness under vacuum, the residue is taken up in water, 2 g. of activated carbon is added thereto, the mixture is filtered, and the filtrate is brought to pH 5 by adding dropwise glacial acetic acid; then, 2 g. of activated carbon is again added, the mixture is filtered, and subsequently precipitated by the addition of concentrated hydrochloric acid to a pH of 1. After extracting the thus-obtained crude product with isopropanol at room temperature, one obtains 7.7 g. (81% of theory) of diglycolic acid di-(3-carboxy-5-chloro-2,4,6-triiodo-N-methylanilide), m.p. 218°–220° (under decomposition).

EXAMPLE 13

3.13 g. of the monopyrrolidide of 5-methylamino-2,4,6-triiodoisophthalic acid is suspended in 10 ml. of dioxane. The mixture is heated to 95°–100°, and a solution of 0.5 g. of diglycolic acid dichloride in 1.2 ml. of dioxane is added dropwise under agitation. The, the mixture is maintained at 95° for 4 hours. After cooling to room temperature, the mixture is diluted with water to 50 ml. The thus-separated precipitate is vacuum-filtered after solidification, washed with water, and dried at 50°. The crude product (2.7 g.) obtained in this manner is recrystallized from methanol.

The final product is 2.2 g. (65% of theory) of diglycolic acid di-(3-carboxy-5-pyrrolidinocarbonyl-1,4,6-triiodo-N-methylanilide), m.p. 270°–271° (under decomposition).

EXAMPLE 14

16.4 g. of 3-methylamino-5-N-butyrolactamyl-2,4,6-triiodobenzoic acid is suspended in 53.6 ml. of dioxane, heated to 95°–100°, and a solution of 2.75 g. of diglycolic acid dichloride in 6 ml. of dioxane is added dropwise thereto within 5 minutes under agitation. Then, the reaction mixture is maintained at 95° for 4 hours. After cooling to room temperature, the mixture is diluted with water to 250 ml. The thus-separated precipitate is vacuum-filtered after solidification, washed with water, and dried at 50°. The thus-obtained crude product (12.9 g.) is suspended in 64.5 ml. of ethanol and dissolved by the addition of 29 ml. of concentrated aqueous monomethylamine solution. After agitation overnight and cooling in ice, the thus-separated monomethylamine salt is vacuum-filtered, dissolved in 120 ml. of water, and 0.6 g. of activated carbon is added for decolorization. After filtration, the solution is brought to pH 1 by adding concentrated hydrochloric acid. After some time, the precipitate is vacuum-filtered, washed with water, and dried at 50°, thus obtaining 9.0 g. (51% of theory) of diglycolic acid di-(3-carboxy-5-N-butyrolactamyl-2,4,6-triiodo-N-methylanilide), m.p. 266°–268° (under decomposition).

EXAMPLE 15

300 g of 3-methylamino-5-acetylaminomethyl-2,4,6-triiodo benzoic acid suspended in 3,7 l dioxane is treated with a solution of 60 g of 3,6-dioxasuberic acid dichloride in 150 ml dioxane as set forth in Example 4. After agitation at 95° for 6 hours and cooling the reaction mixture is poured into 3 l of ice water and the thus-separated precipitate is filtered and washed with 500 ml acetone. Thereafter the precipitate is dissolved in water as sodium salt and decolorized by treatment with activated carbon. After precipitation with hydrochloric acid, 210 g (62 % of theory) of 3,6-dioxasuberic acid di-(3- carboxy-5-acetylaminomethyl-2,4,6-triiodo-N-methylanilide) is obtained, m.p. 233° –239° (under decomposition). If 3,6,9-trioxaundecandioxic acid dichloride is used instead of 3,6-dioxasuberic acid dichloride, after treatment with acetone 80% of theory of 3,6,9-trioxaundecandioic acid di-(3-carboxy-5-acetylaminomethyl-2,4,6-triiodo-N-methylanilide) is obtained, m.p. 201° – 215° C (under decomposition).

EXAMPLE 16

300 g of 3-methylamino-2,4,6-triiodobenzoic acid suspended in 3,9 l toluene is treated with a solution of 65,1 g of 3,6-dioxasuberic acid dichloride in 100 ml toluene for 2,5 hours at the boiling point as set forth in Example 11. The precipitated crude product is filtered off and treated with 500 ml acetone. The reaction product is suspended in a solution of 0,7 l water and 0,7 ml methanol, dissolved by the addition of semiconcentrated sodium hydroxide solution, and decolorized by treatment with activated carbon. After precipitation with hydrochloric acid 227 g (66% of therory) of 3,6-dioxasuberic acid di-(3-carboxy-2,4,6-triiodo-N-methylanilide) is obtained, m.p. 268° – 275° (under decomposition).

EXAMPLE 17

Preparation of a Solution Ready for Use:

EXAMPLE 17

| Preparation of a Solution Ready for Use: | |
|---|---|
| Diglycolic acid di-(3-carboxy-2,4,6-triiodo-N-methylanilide) | 425.0 g. |
| N-Methylglucamine | 143.5 g. |
| Disodium salt of ethylenediamine-N-N'-tetraacetic acid | 0.1 g. |
| Aqua bidestillata ad | 1000 ml. |

The salt solution is prepared in accordance with the above recipe, adjusted to pH 7.0 ± 0.2, filled into ampoules of 10 and 20 ml., respectively, and sterilized. Iodine content: 280 mg./ml.

EXAMPLE 18

Preparation of a Solution Ready for Use:

EXAMPLE 18

| Preparation of a Solution Ready for Use: | |
|---|---|
| 3,6,9-Trioxaundecandioic acid di-(3-carboxy-5-acetylaminomethyl-2,4,6-triiodo-N-methylanilide) | 591.6 g |
| N-Methylglucamine | 166.5 g |
| Disodium salt of ethylenediamine-N,N'-tetraacetic acid | 0.4 g |
| Aqua bidestillata ad | 1000 ml |

The salt solution is prepared in accordance with the above recipe, adjusted to pH 7 ± 0,5, filled into bottles or ampoules and sterilized. Iodine content: 325 mg/ml.

EXAMPLE 19

Preparation of a Solution Ready for Use:

EXAMPLE 19

| Preparation of a Solution Ready for Use: | |
|---|---|
| Diglycolic acid di-(3-carboxy-5-acetylaminomethyl-2,4,6-triiodo-N-methylanilide) | 256.0 g. |
| N-Methylglucamine | 40.0 g. |
| Sodium hydroxide | 7.8 g. |
| Disodium salt of ethylenediamine-N,N'-tetraacetic acid | 0.1 g. |
| Aqua bidestillata ad | 1000 ml. |

The salt solution is prepared in accordance with the above recipe, adjusted to pH 7.0 ± 0.2, filled into bottles of 100 ml., and sterilized. Iodine content: 150 mg./ml.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A triiodized N-methyldicarboxylic acid anilide of the formula

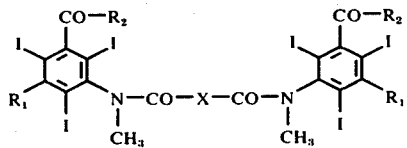

wherein $R_1$ is hydrogen or halogen, carboxyl, $R_2$ is chlorine, hydroxy, lower alkoxy, hydroxyalkoxy or alkoxyalkoxy, alkoxy in each instance being of 1–6 carbon atoms; and X is alkylene of 2–14 carbon atoms interrupted by at least one oxygen atom, or a physiologically acceptable salt thereof.

2. A compound of claim 1, wherein $R_1$ is hydrogen.
3. A compound of claim 1, wherein $R_1$ is halogen.
4. A compound of claim 1, wherein $R_1$ is carboxyl.
5. A compound of claim 1, wherein X is alkylene of 2–6 carbon atoms interrupted by a single oxygen atom.
6. A compound of claim 1, wherein X is alkylene of 2–14 carbon atoms interrupted at every second or third carbon atom by an oxygen atom.
7. A compound according to claim 1, diglycolic acid di-(3-chlorocarbonyl-2,4,6-triiodo-N-methylanilide).
8. A compound according to claim 1, diglycolic acid di-(3-carboxy-2,4,6-triiodo-N-methyl-anilide).
9. A compound according to claim 1, 3,6,9-trioxaundecanedioic acid di-(3-carboxy-2,4,6-triiodo-N-methylanilide).
10. A compound according to claim 1,, diglycolic acid di-(3-methoxycarbonyl-2,4,6-triiodo-N-methylanilide).
11. A compound according to claim 1, diglycolic acid di-(3,5-dicarboxy-2,4,6-triiodo-N-methylanilide).
12. A compound according to claim 1, 4,7,10,13-tetraoxahexadecane-1,16-dioic acid di-(3-carboxy-2,4,6-triiodo-N-methylanilide).
13. A compound according to claim 1, diglycolic acid di-(3-carboxy-5-chloro-2,4,6-triiodo-N-methylanilide).
14. A compound according to claim 1, 3,6-dioxasuberic acid di-(3-carboxy-2,4,6-triiodo-N-methylanilide).

* * * * *